(12) United States Patent
Suzuki et al.

(10) Patent No.: US 8,791,317 B2
(45) Date of Patent: Jul. 29, 2014

(54) ABSORBENT ARTICLE AND METHOD OF MANUFACTURING ABSORBENT ARTICLE

(75) Inventors: Nahomi Suzuki, Kagawa (JP); Koichi Yamaki, Kagawa (JP)

(73) Assignee: Unicharm Corporation, Ehime (JP)

( * ) Notice: Subject to any disclaimer, the term of this patent is extended or adjusted under 35 U.S.C. 154(b) by 889 days.

(21) Appl. No.: 12/990,282

(22) PCT Filed: Apr. 27, 2009

(86) PCT No.: PCT/JP2009/058307
§ 371 (c)(1),
(2), (4) Date: Mar. 3, 2011

(87) PCT Pub. No.: WO2009/133864
PCT Pub. Date: May 11, 2009

(65) Prior Publication Data
US 2011/0144607 A1    Jun. 16, 2011

(30) Foreign Application Priority Data

Apr. 30, 2008    (JP) .................. 2008-119415

(51) Int. Cl.
*A61F 13/15* (2006.01)
*A61F 13/514* (2006.01)

(52) U.S. Cl.
CPC ..... *A61F 13/51405* (2013.01); *A61F 13/51484* (2013.01); *A61F 2013/51433* (2013.01); *A61F 2013/5147* (2013.01)
USPC ......................................... 604/365; 604/382

(58) Field of Classification Search
CPC ............ A61F 13/514; A61F 13/51405; A61F 13/51474; A61F 13/51484; A61F 2013/51433; A61F 2013/5147
USPC ................................. 604/365, 382
See application file for complete search history.

(56) References Cited

U.S. PATENT DOCUMENTS

| | | | | |
|---|---|---|---|---|
| 3,702,610 A | * | 11/1972 | Sheppard et al. | 604/361 |
| 5,300,358 A | * | 4/1994 | Evers | 442/396 |
| 6,432,095 B1 | | 8/2002 | Wada et al. | |
| 6,747,186 B2 | * | 6/2004 | Shimizu | 604/364 |
| 7,432,412 B2 | * | 10/2008 | Kigata et al. | 604/367 |
| 2003/0124308 A1 | * | 7/2003 | Cree et al. | 428/137 |

FOREIGN PATENT DOCUMENTS

| | | |
|---|---|---|
| CN | 1298691 A | 6/2001 |
| EP | 2 292 201 A1 | 3/2011 |
| JP | 5-41527 U | 6/1993 |
| JP | 2001-145669 A | 5/2001 |
| JP | 2002-53170 A | 2/2002 |

(Continued)

OTHER PUBLICATIONS

English language translation of JP 2005-118533 A.*

(Continued)

*Primary Examiner* — Lynne Anderson
(74) *Attorney, Agent, or Firm* — Brinks Gilson & Lione

(57) ABSTRACT

An absorbent article that includes a water-disintegratable top sheet, a water-disintegratable back sheet, and a water-disintegratable absorber interposed between the top sheet and the back sheet. Adhesive coating regions of an adhesive are formed in the back sheet, and the coating regions of the adhesive are provided to continuously extend from one face of the back sheet to the other face of the back sheet.

3 Claims, 4 Drawing Sheets

(56) References Cited

FOREIGN PATENT DOCUMENTS

| JP | 2004-344443 | | 12/2004 |
|---|---|---|---|
| JP | 2005-118533 | A | 3/2005 |
| JP | 2008-119415 | A | 5/2008 |
| WO | WO 2006/071159 | A1 | 7/2006 |

OTHER PUBLICATIONS

Official Action and English translation from corresponding Chilean application No. 1043-2009 mailed Mar. 7, 2013, (10 pages).
International Search Report from corresponding PCT application No. PCT/JP2009/058307 dated Aug. 11, 2009, 2 pages.
Official Action and English translation from corresponding Chinese application No. 200980115678.1 issued May 17, 2013, (6 pages).
Official Action from corresponding Australian application No. 2009240979 issued Jul. 24, 2013 (3 pgs).
Official Action and English translation from corresponding JP application No. 2008-119415 mailed Oct. 2, 2012, (8 pages).
Official Action and English translation from corresponding CN application No. 2009801156781 issued Oct. 10, 2012 (9 pages).
European extended Search Report from cooresponding European Application No. 09738801.1.

* cited by examiner

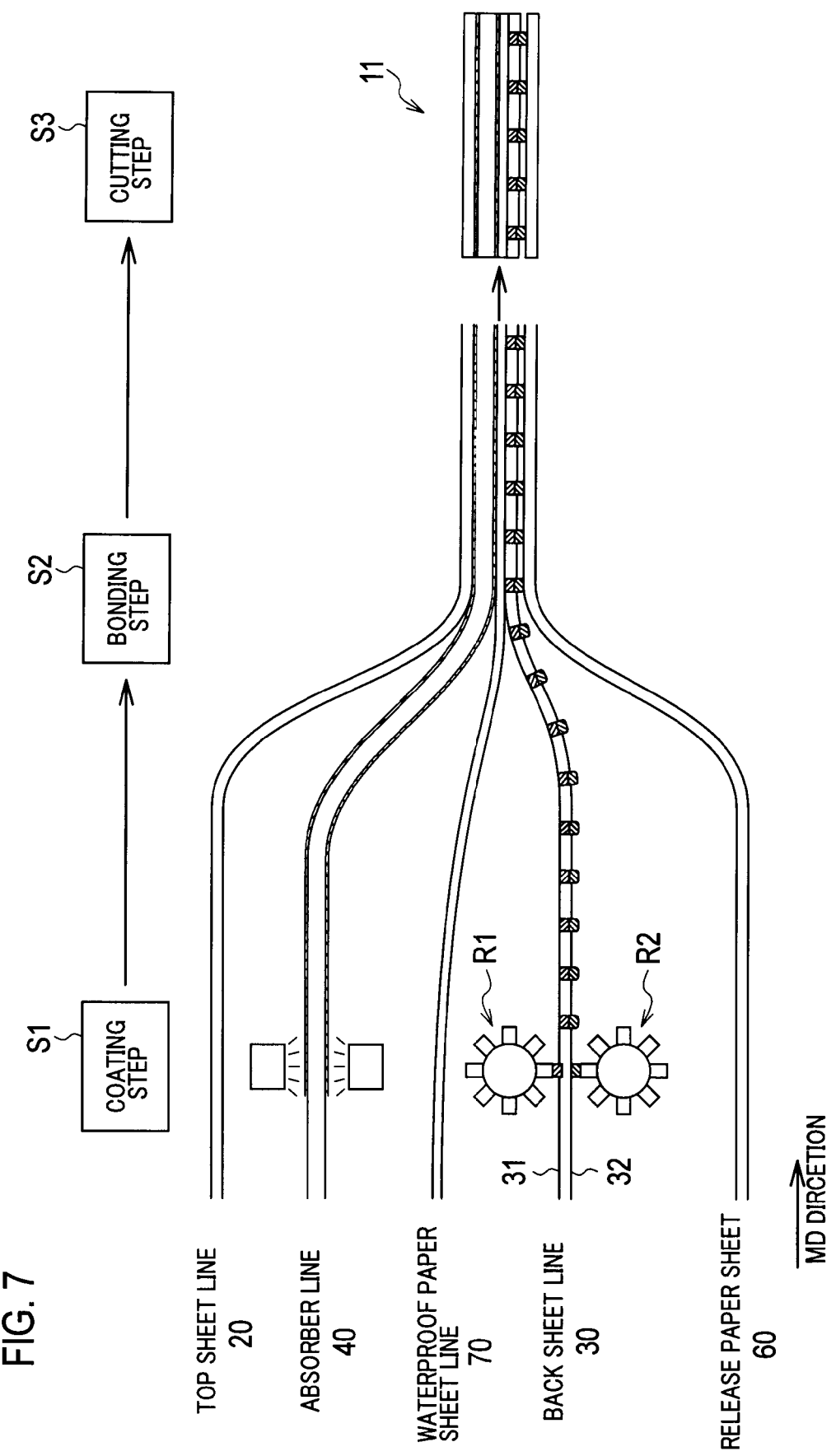

ABSORBENT ARTICLE AND METHOD OF MANUFACTURING ABSORBENT ARTICLE

RELATED APPLICATION

This application is a 35 U.S.C. §371 national phase filing of International Patent Application No. PCT/JP2009/058307 filed Apr. 27, 2009, to which priority is claimed under 35 U.S.C. §120 and through which priority is claimed under 35 U.S.C. §119 to Japanese Patent Application No. 2008-119415, filed Apr. 30, 2008.

BACKGROUND OF THE INVENTION

1. Field of the Invention

The present invention relates to an absorbent article including a water-disintegratable top sheet, a water-disintegratable back sheet, and a water-disintegratable absorber interposed between the top sheet and the back sheet. The present invention also relates to a method of manufacturing the absorbent article.

2. Description of the Related Art

As absorbent articles such as pantyliners and sanitary napkins, absorbent articles that are formed of a water-disintegratable (water-decomposable) material and that disperse in water when flushed in a toilet have been known (see, for example, Patent Document 1).

Typically, such an absorbent article includes a water-disintegratable top sheet, a water-disintegratable back sheet, and a water-disintegratable absorber interposed between the top sheet and the back sheet.

A coating of an adhesive is applied to an outer side of the back sheet to be in contact with underwear. When a wearer attaches the absorbent article to the underwear, the absorbent article is fixed to the underwear by bonding the adhesive to the underwear.

Patent Document 1: Japanese Patent Application Publication No. 2001-145669

SUMMARY OF THE INVENTION

In the absorbent article as described above, a nonwoven fabric or the like is used as a material for the water-disintegratable back sheet. Accordingly, the water-disintegratable back sheet has a low adhesion with the adhesive, compared with a non-water-disintegratable back sheet formed of a material such as polyethylene.

For this reason, a problem arises that the adhesive is separated from the back sheet and remains on the underwear when the water-disintegratable absorbent article is peeled off from the underwear.

The present invention has been made in consideration of the above problem, and an objective of the present invention is to provide an absorbent article and a method of manufacturing the absorbent article which prevent an adhesive from being separated from a back sheet when the absorbent article is peeled off from underwear.

A first characteristic of the present invention is summarized as an absorbent article including a water-disintegratable top sheet, a water-disintegratable back sheet, and a water-disintegratable absorber interposed between the top sheet and the back sheet. In the absorbent article, adhesive coating regions are formed in the back sheet, and the adhesive coating regions are provided to continuously extend from one face of the back sheet to the other face of the back sheet.

In the first characteristic of the present invention, the adhesive coating regions are formed intermittently in planar directions of the back sheet, and an interval between adjacent ones of the adhesive coating regions may be longer than a maximum length of fibers in the back sheet.

In the first characteristic of the present invention, the adhesive coating regions are formed to continuously extend from a face of the back sheet on an absorber side, to a face of the back sheet on a surface side to be in contact with underwear. Areas of the adhesive coating regions at the face of the back sheet on the absorber side may be larger than areas of the adhesive coating regions at the face of the back sheet on the surface side to be in contact with underwear.

In the first characteristic of the present invention, to the adhesive coating regions, a first adhesive may be applied from the absorber 4 side of the back sheet, and a second adhesive may be applied from the surface side of the back sheet to be in contact with underwear.

A second characteristic of the present invention is summarized as a method of manufacturing an absorbent article including a water-disintegratable top sheet, a water-disintegratable back sheet, and a water-disintegratable absorber interposed between the top sheet and the back sheet. The method includes: a coating step of applying a first adhesive and a second adhesive to predetermined regions in a continuously-fed lengthy continuum of the back sheets, the first adhesive being applied by a first roller from an absorber side of the back sheet, the second adhesive being applied by a second roller from a surface side of the back sheet to be in contact with underwear; and a bonding and cutting step of bonding a continuously-fed lengthy continuum of the top sheets, a continuously-fed lengthy continuum of the absorbents, and the continuum of the back sheets together, and then cutting the continua in a predetermined length.

BRIEF DESCRIPTION OF THE DRAWINGS

FIG. 7 is a diagram illustrating an absorbent article manufacturing method according to the second embodiment of the present invention.

DETAILED DESCRIPTION OF THE PREFERRED EMBODIMENTS (Absorbent Article According to First Embodiment)

Figure 1:
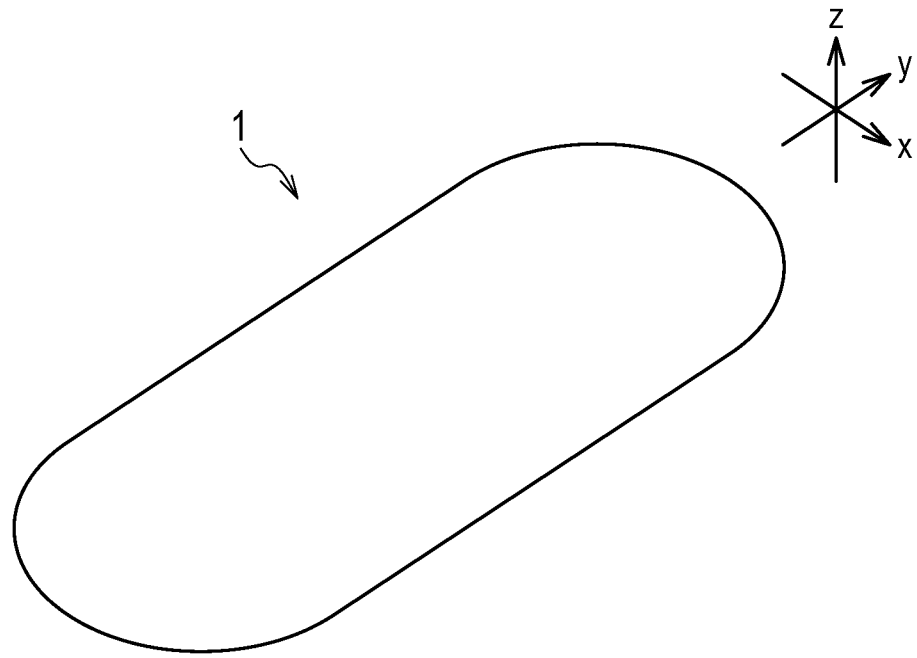
FIG. 1 is a perspective diagram of an absorbent article according to a first embodiment of the present invention viewed from a top sheet side.
Figure 2:
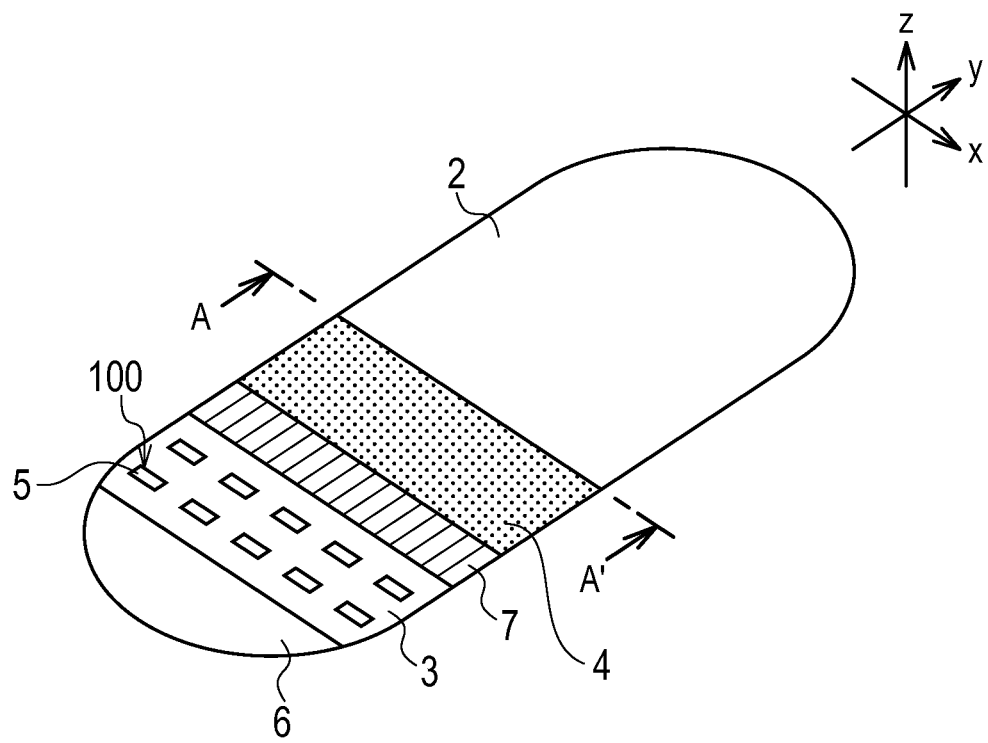
FIG. 2 is a perspective diagram illustrating the configuration of the absorbent article according to the first embodiment of the present invention.
Figure 3:
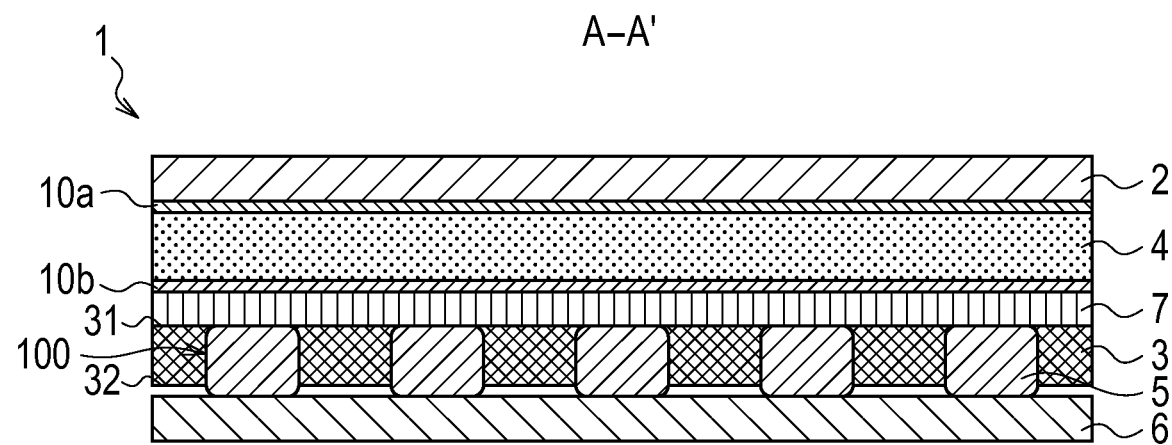
FIG. 3 is a cross-sectional diagram of an endothermic material of the absorbent article according to the first embodiment of the present invention.

With reference to FIGS. 1 to 3, a description will be given of an absorbent article according to a first embodiment of the present invention. FIG. 1 is a perspective diagram of an absorbent article 1 according to the first embodiment of the present invention viewed from a top sheet side (described later) to be in contact with the skin surface of a wearer. FIG. 2 is a diagram illustrating the configuration of the absorbent article 1 of the present invention. FIG. 3 is a cross-sectional diagram taken along the A-A line in the absorbent article 1 of FIG. 2. Note that, as shown in FIGS. 1 to 3, the width direction, the longitudinal direction, and the thickness direction of the absorbent article 1 are shown as an X-axis direction, a Y-axis direction, and a Z-axis direction, respectively in this embodiment. In addition, planar directions of the absorbent article 1 indicate the X-axis direction and the Y-axis direction.

The absorbent article 1 according to the present embodiment is a water-disintegratable absorbent article used as, for example, a pantyliner or a sanitary napkin. The water-disintegratable absorbent article is an absorbent article formed to disperse by the flow and pressure of water when flushed in a toilet or the like.

As shown in FIG. 2, the absorbent article 1 according to the present embodiment includes a water-disintegratable top sheet 2, a water-disintegratable back sheet 3, a water-disintegratable absorber 4 interposed between the top sheet 2 and the back sheet 3, and a waterproof paper sheet 7.

In addition, as shown in FIG. 2, coatings of water-disintegratable or water-soluble adhesives 10a and 10b are applied to the absorber 4 on its surface facing the top sheet 2 and on its surface facing the back sheet 3 in the thickness direction, respectively. The top sheet 2 is bonded to the absorber 4 with the adhesive 10a applied to the absorber 4. The back sheet 3 is bonded to the absorber 4 with the adhesive 10b applied to the absorber 4.

The top sheet 2 has liquid permeability. The top sheet 2 is preferably made of a hydrophilic material which does not irritate the skin. Specifically, the top sheet 2 may be made of a material using water-disintegratable nonwoven fibers alone. Alternatively, in order to prevent breaking due to falling off of the fibers, the top sheet 2 may be made of a material using mainly cellulose hydrophilic fibers.

An example of the hydrophilic fibers used as the top sheet 2 is formed as follows. First, hydrophilic fibers and small-diameter hydrophobic fibers are mixed with a weight ratio of 80 to 100% to 0 to 20%, and are adjusted to be in the 20 g/m$^2$ to 50 g/m$^2$ range. Thereafter, the fibers are entwined with each other by hydroentangling. Then, the resultant fibers are dried and adjusted to have a thickness in the 0.3 mm to 1.0 mm range and a fiber length in the 1 to 20 mm range. A wetlaid spunlace nonwoven fabric thus obtained can be used as the top sheet 2.

Alternatively, the wetlaid spunlace nonwoven fabric formed of 30% unbeaten pulp, 20% extra-small-diameter splittable fibers, and rayon having a fineness of 1.1 dtex and a fiber length of 9 mm, and adjusted to have a basis weight of 40 g/m$^2$ may be used as the top sheet 2.

The absorber 4 is configured to hold body fluid excreted from the wearer. A material, holding the body fluid, such as a water-disintegratable nonwoven fabric, water-disintegratable airlaid pulp, or a water-disintegratable paper sheet can be used for the absorber 4. For example, water-disintegratable airlaid pulp obtained by mixing 80% pulp and 20% water-disintegratable binder and adjusted to have a basis weight of 70 g/m$^2$ may be used as a material for the absorber 4.

In the absorbent article 1, the back sheet 3 is a part to be positioned on the underwear. A water-disintegratable nonwoven fabric, a water-disintegratable paper sheet including water-dispersible fibers, or the like is used as a material for the back sheet 3. For example, a water-disintegratable nonwoven fabric, and water-disintegratable paper sheets as shown in the following can be listed.

(1) A water-disintegratable nonwoven fabric obtained by subjecting water-dispersable fibers each having a relatively short fiber length to water-jet processing in order to entangle the fibers.

(2) A water-disintegratable paper sheet formed by using water-dispersable fibers, such as pulp or rayon, as a material, bonding the fibers to each other with a water-soluble binder, and then forming the fibers into a sheet.

(3) A water-disintegratable paper sheet formed by using pulp as a material, and forming the pulp into a sheet by bonding the pulp fibers to each other by hydrogen bonds.

(4) A water-disintegratable paper sheet formed into a sheet by causing water-dispersable fibers to be entangled.

In order to resist fluid smearing, the side of the back sheet 3 to be in contact with the underwear may be subjected to water-repellent processing by applying, to the skin-contact side, a biodegradable resin, such as a polylactic resin or a polyvinylalcohol resin.

For example, a wetlaid spunlace formed as follows can be used as the back sheet 3. Firstly, pulp fibers and rayon are mixed at a weight ratio of 30 to 70% to 30 to 70%, and the mixture is adjusted to have a basis weight in the 20 g/m$^2$ to 50 g/m$^2$ range. Thereafter, the fibers are entwined with each other by hydroentangling. Then, the resultant fibers are dried and adjusted to have a thickness in the 0.1 mm to 1.0 mm range and a fiber length in the 1 to 20 mm range.

Specifically, a wetlaid spunlace nonwoven fabric formed of 30% beaten pulp, 20% unbeaten pulp, and rayon having a fineness of 1.1 dtex and a fiber length of 7 mm and adjusted to have a basis weight of 40 g/m$^2$ can be used as the back sheet 3.

Further, a coating of an adhesive 5 is applied to the back sheet 3 in order to fixedly adhere the absorbent article 1 to the underwear of the wearer. Note that a detailed description will be given later of the configuration of the adhesive 5.

The waterproof paper sheet 7 is interposed between the absorber 4 and the back sheet 3. When the absorber 4 or the back sheet 3 has low liquid impermeability, the waterproof paper sheet 7 is interposed to compensate for their lacking liquid impermeability.

A water-disintegratable paper sheet to which a water-soluble resin is applied or a water-soluble nonwoven fabric is used as a material for the waterproof paper sheet 7. In addition, a coating of a water repellent having a concentration not inhibiting the water disintegratability may be applied. Assume, for example, that the absorber 4 is formed of water-disintegratable air-laid pulp having a basis weight of 40 g/m$^2$, and that the back sheet 3 is formed of a non-water-repellent wetlaid spunlace nonwoven fabric adjusted to have a basis weight of 40 g/m$^2$, made of 30% beaten pulp, 20% unbeaten pulp, and rayon having a fineness of 1.1 dtex and a fiber length of 7 mm. In this case, the absorbent article 1 has low liquid impermeability, and accordingly, a water-disintegratable nonwoven fabric having a basis weight of 40 g/m$^2$, the surface of which is processed with a paraffinic water repellent, may be added.

Note that the absorbent article 1 does not have to be provided with the waterproof paper sheet 7 when the absorber 4 or the back sheet 3 has liquid impermeability.

Further, as shown in FIGS. 2 and 3, the absorbent article 1 according to the present embodiment has a release paper sheet 6 for preserving the adhesion of the adhesive 5. The release paper sheet 6 is peeled off when the absorbent article 1 is used.

Next, a description will be given of the adhesive 5 applied to the back sheet 3 in the absorbent article 1 according to the present embodiment.

In the absorbent article 1 according to the present embodiment, coating regions 100 of the adhesive 5 are formed in the back sheet 3 to allow the absorbent article 1 to be fixedly attached to the underwear of the wearer. The coating regions 100 of the adhesive 5 are formed to continuously extend from one face to the other face of the back sheet 3.

Specifically, as shown in FIG. 3, the coating regions 100 of the adhesive 5 are formed to continuously extend in the thickness direction from a face (one face) 31 of the back sheet 3 on an absorber 4 side to a face 32 (the other face) of the back sheet 3 on a surface side to be in contact with the underwear. In other words, the coating regions 100 of the adhesive 5 are formed to extend from the face 31 of the back sheet 3 on the absorber 4 side to the face 32 of the back sheet 3 on the underwear contact side through the inside of the back sheet 3.

The coating regions 100 of the adhesive 5 include the material of the back sheet 3 (e.g., fibers of a non-woven fabric) and the adhesive 5. Specifically, the coating regions 100 of the adhesive 5 are formed by causing the adhesive 5 to permeate into the gaps (between the fibers) in the material of the back sheet 3 (e.g., the fibers of a non-woven fabric).

For example, a coating of the adhesive 5 in a state of having a low consistency is applied to the back sheet 3, and then hardens as permeating through between the fibers of the back sheet 3. Thereby, the coating regions 100 of the adhesive 5 can physically fixate between the fibers of the back sheet 3. Accordingly, the interlayer strength (strength between the fibers) of the back sheet 3 can be improved.

The methods for extending the coating regions 100 of adhesive 5 through the back sheet 3 include: a method of shortening the open time of the adhesive 5 by using direct coating, a method of increasing a pickup amount of the adhesive 5 by designing the etching roll of a roll coater to have a deep cell, a method of causing the adhesive 5 to permeate the back sheet 3 by applying pressure to the back sheet 3 from both sides thereof while rolling the back sheet 3 between nip rolls after application of the adhesive 5 to the back sheet 3.

The amount of the adhesive 5 for each coating region 100 of the adhesive 5 is preferably within a range of 10 $g/m^2$ to 250 $g/m^2$, and more specifically, within a range of 50 $g/m^2$ to 150 $g/m^2$.

When, for example, the amount of the adhesive for each coating region 100 of the adhesive 5 is less than 50 $g/m^2$, most of the adhesive 5 permeates into the back sheet 3. Thus, only a little amount of the applied adhesive 5 remains on the back sheet 3 on the underwear contact side, whereby the adhesive 5 tends to have only low adhesion with the underwear. Accordingly, such amount is not preferable. On the other hand, if the weight is more than 150 $g/m^2$, an excessive amount of the adhesive 5 which does not permeate into the back sheet 3 remains on the back sheet 3. This results in high adhesion between the adhesive 4 and the underwear, and possibly a fracture of the adhesive 5. Accordingly, such amount is not preferable.

Used as a material for the adhesive 5 includes: a pressure-sensitive adhesive formed mainly of a synthetic rubber of styrene-ethylene-butadiene-styrene block copolymer (SEBS), styrene-butadiene-styrene block copolymer (SBS), styrene-isoprene-styrene block copolymer (SIS), and the like; and a thermo-sensitive adhesive formed mainly of a synthetic rubber of EVA and the like. Alternatively, a biodegradable adhesive or a water-soluble adhesive may be used.

No matter which of the above-given materials is used, the back sheet 3 can disperse at portions where no coating region 100 of the adhesive 5 is formed.

Figure 4:
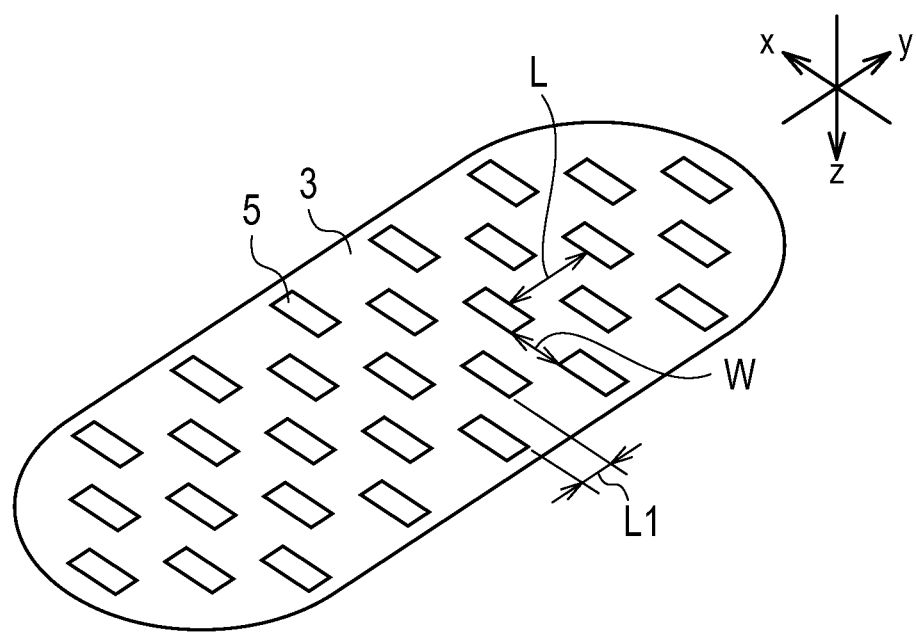
FIG. 4 is a perspective diagram of the absorbent article according to the first embodiment of the present invention viewed from a back sheet side.

As shown in FIG. 4, in the absorbent article 1 according to the present embodiment, the coating regions 100 of the adhesive 5 are arranged intermittently in the planar directions on the face 32 of the underwear-contact back sheet 3. Specifically, as shown in FIG. 4, the coating regions 100 of the adhesive 5 are formed by intermittent applications at intervals L in the longitudinal direction of the back sheet 3, and at intervals W in the width direction of the back sheet 3. The coating regions 100 of the adhesive 5 are preferably scattered throughout the underwear contact face 32 of the back sheet 3. In addition, the coating regions 100 of the adhesive 5 are preferably formed by applications at regular intervals in the longitudinal direction and the width direction.

Furthermore, in the absorbent article 1 according to the present embodiment, the interval between adjacent ones of the coating regions 100 of the adhesive 5 is longer than a maximum length of the fibers in the back sheet 3. Specifically, as shown in FIG. 4, the coating regions 100 are formed so that an interval L1 between adjacent ones of the coating regions 100 may be longer than the lengths of fibers of a nonwoven fabric serving as a material for the back sheet 3 in the planar directions of the back sheet 3. This design makes it possible to prevent the adhesive 5 at one region from being connected to the adhesive 5 at another region by the fibers when the back sheet 3 disperses in water.

Figure 5:
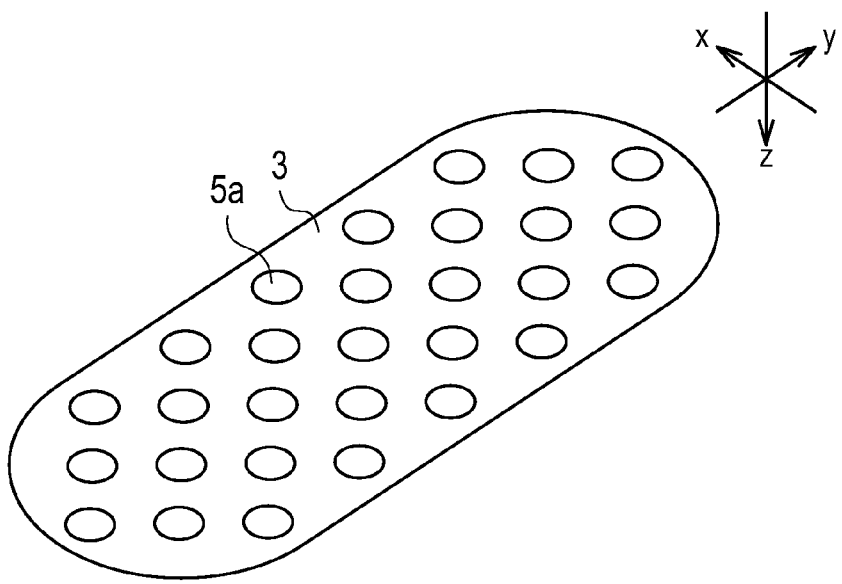
FIG. 5 is a perspective diagram of an absorbent article according to a modification of the present invention viewed from a back sheet side.

The coating regions 100 of the adhesive 5 may be shaped into square as shown in FIG. 4, and circular as shown in an example in FIG. 5. Further, the coating regions 100 of the adhesive 5 may be oval, gourd-shaped, square, rectangular, drop-shaped, or the like. The dimension of each coating region 100 of the adhesion 5 in planer directions is, for example, 1 to 10 mm length sides in a square, or a 1 to 10 mm diameter in a circle.

The methods of forming the coating regions 100 of the adhesive 5 by intermittent applications on the back sheet 3 include: a slot coating method, a spray coating method, a porous coating method, a roll coater method, a gravure method, and other methods. Note that, it is preferable to use the roll coater method, among the above-given methods, because of its capability of designing intermittent patterns.

In the absorbent article 1 according to the first embodiment of the present invention, the coating regions 100 of the adhesive 5 are formed to continuously extend from the face 31 of the back sheet 3 on the absorber 4 side to the face 32 of the back sheet 3 on the underwear contact side.

This makes the adhesive 5 and the back sheet 3 bond more strongly, allowing the adhesive 5 to be resistant to detaching from the back sheet 3.

In this manner, the absorbent article 1 of the present invention makes it possible to prevent the adhesive 5 from being separated from the back sheet 3 when the absorbent article 1 is peeled off underwear.

In a case where the back sheet 3 is formed of a multiple-layered nonwoven fabric, if the interlayer strength of the back sheet 3 is weak, the nonwoven fabric of the back sheet 3 separates at its layers (interlayer separation) when the wearer peels the absorbent article 1 off the underwear, in other words, when a force in a peeling direction is applied. As a result, part of the nonwoven fabric and the adhesive 5 remain on the underwear.

In the absorbent article 1 according to the present invention, however, the adhesive 5 inside of the back sheet 3 fixates the fibers of the back sheet 3 to improve the interlayer strength of the back sheet 3. Accordingly, part of the back sheet 3 and the adhesive 5 can be prevented from remaining on the underwear.

Additionally, in the absorbent article 1 according to the first embodiment of the present invention, the adhesive 5 can be used as an assembling adhesive for bonding the back sheet 3 and the absorber 4 together when the coating regions 100 of the adhesive 5 penetrates the back sheet 3 and is exposed to the surface on the absorber 4 side.

Further, in the absorbent article 1 according to the first embodiment of the present invention, an interval between adjacent ones of the coating regions 100 of the adhesive 5 in the planer directions of the back sheet 3 is longer than the maximum length of the fibers in the back sheet 3.

Consequently, in the absorbent article 1, a physical impact, such as water pressure, can easily disperse fibers in between the coating regions 100 of the adhesive 5. Further, the material for the back sheet 3 does not necessarily have to be a water-soluble or biodegradable material, the quality of which is easily affected due to conditions of temperature, humidity, and the like.

(Modification)

A modification of the present invention will be described, focusing on differences from the first embodiment described above.

In an absorbent article according to the modification of present embodiment, the coating regions 100 of the adhesive 5 are formed to continuously extend from the face 31 of the back sheet 3 on the absorber 4 side to the face 32 of the back sheet 3 on the underwear contact surface side, and to be exposed from the face 31 of the back sheet 3 on the absorber 4 side.

Moreover, in the absorbent article 1 of the modification, the coating regions 100 of the adhesive 5 are formed so that their areas at the face 31 of the back sheet 3 on the absorber 4 side are larger than the areas at the face 32 of the back sheet 3 on the underwear contact side.

The absorbent article having such a structure can make the adhesion of bonding the back sheet 3 and the absorber 4 larger than the adhesion of bonding the back sheet 3 and underwear.

Accordingly, it can be reliably prevented that the adhesive 5 is separated from the back sheet 3 and remains on underwear, when the absorbent article 1 is peeled off the underwear. Furthermore, it can also be prevented that the back sheet 3 remains on underwear due to separation of the back sheet 3 and the absorber 4 when the absorbent article 1 is peeled off the underwear.

(Absorbent Article According to Second Embodiment)

Figure 6:
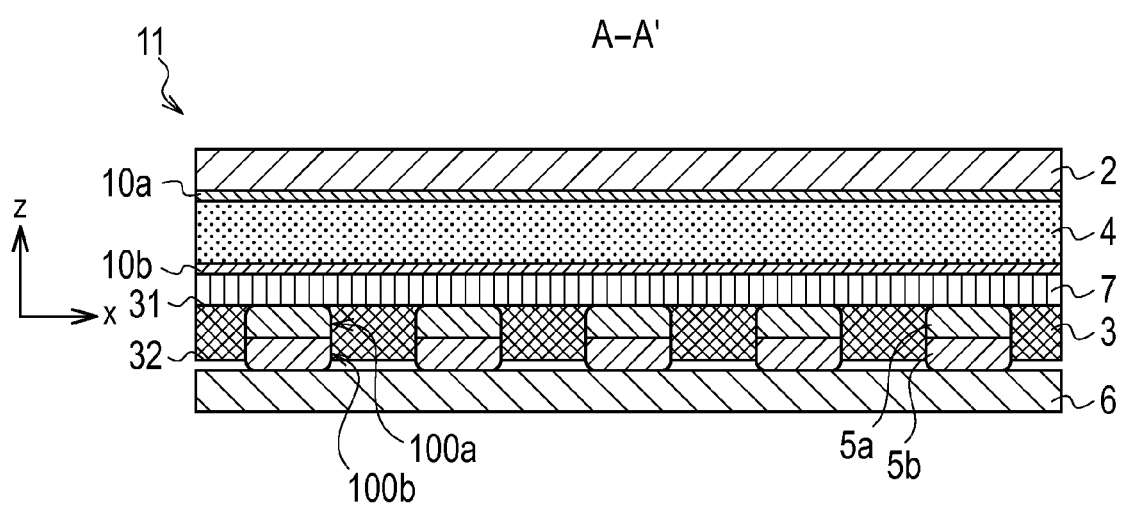
FIG. 6 is a cross-sectional diagram of an endothermic material of an absorbent article according to a second embodiment of the present invention.

With reference to FIG. 6, a description will be given of an absorbent article according to a second embodiment of the present invention. The absorbent article according to the second embodiment of the present invention will be described below, focusing on differences from the absorbent article according to the first embodiment of the present invention. FIG. 6 is a cross-sectional diagram of an absorbent article 11 according to the second embodiment.

The absorbent article 11 according to the present embodiment has the same structure as the absorbent article according to the first embodiment, except for the structure of the coating regions 100 of the adhesive 5 formed in the back sheet 3.

As shown in FIG. 6, in the absorbent article 11, the coating regions 100 of the adhesive 5 are formed of coating regions 100a of a first adhesive 5a and coating regions 100b of a second adhesive 5b so as to penetrate the back sheet 3.

In the absorbent article 11 according to the present embodiment, in the coating regions 100 of the adhesive 5, a coating of the first adhesive 5a is applied from the absorber 4 side of the back sheet 3, and a coating of the second adhesive 5b is applied from the underwear contact surface side of the back sheet 3.

The coating regions 100a of the first adhesive 5a are regions where the first adhesive 5a is applied from the face 31 of the back sheet 3 on the absorber 4 side, and the coating regions 100b of the second adhesive 5b are regions where the second adhesive 5b is applied from the face 32 of the back sheet 3 on the underwear contact side. The first adhesive 5a and the second adhesive 5b are applied at the almost same position in the planar directions of the back sheet 3. The coating regions 100 of the adhesive 5 are formed by bonding the coating regions 100a of the first adhesive 5a and the coating regions 100b of the second adhesive 5b together in the width direction.

In the absorbent article 11, a coating of the first adhesive 5a is applied from the face 31 of the back sheet 3 on the absorber 4 side, and a coating of the second adhesive 5b is applied from the face 32 of the back sheet 3 on the underwear contact side. Accordingly, the coating regions 100 of the adhesive 5 are formed in the back sheet 3 in such a state that the adhesive 5 permeates more into the back sheet 3.

Accordingly, in the absorbent article 11, the adhesive 5 can be prevented from being separated from the back sheet 3 when the absorbent article 11 is peeled off underwear.

Additionally, in the absorbent article 11, the adhesive 5 can be used as an assembling adhesive for bonding the back sheet 3 and the absorber 4 together.

Incidentally, the coating regions 100 of the adhesive 5 may be formed so that the areas of the coating regions 100a of the first adhesive 5a at the face 31 of the back sheet 3 on the absorber 4 side may be larger than the areas of the coating regions 100b of the second adhesive 5b at the face 32 of the back sheet 3 on the underwear contact side.

Such a structure makes it possible to reliably prevent the adhesive 5 from being separated from the back sheet 3 and remaining on underwear, when the absorbent article 11 is peeled off the underwear. Furthermore, it can also be prevented that the back sheet 3 remains on underwear due to separation of the back sheet 3 and the absorber 4 when the absorbent article 11 is peeled off the underwear.

(Manufacturing Method of Absorbent Article According to Second Embodiment)

With reference to FIG. 7, a description will be given of a manufacturing method of an absorbent article 11 according to the second embodiment of the present invention.

With the manufacturing method of the absorbent article 11 according to the second embodiment of the present invention, the absorbent article 11 (see FIG. 6) can be manufactured, which includes the liquid-permeable top sheet 2, the liquid-impermeable back sheet 3, and the absorber 4 interposed between the top sheet 2 and the back sheet 3. Note that FIG. 7 describes an example of a case where a machine feeding direction MD of the absorbent article 11 is parallel to the width direction of the absorbent article 11, but the direction is not limited to such a case.

As shown in FIG. 7, at Step 1 (coating step), with respect to a continuously-fed lengthy continuum of the absorbers 4 in an absorber line 40, coatings of the water-disintegratable or water-soluble adhesive 10a and 10b are applied to a face of the absorber 4 on the top sheet 2 side and a face of the absorber 4 on the back sheet 3 side, respectively.

Meanwhile, to predetermined coating regions on a continuously-fed lengthy continuum of the back sheets 3 in a back sheet 3 line, a coating of the first adhesive 5a is applied from the absorber 4 side of the back sheet 3 by a first roller R1, and a coating of the second adhesive 5b is applied from the underwear contact surface side of the back sheet 3 by a second roller R2.

Specifically, in the back sheet 3 line, coatings of the first adhesive 5a and the second adhesive 5b are applied, at the same position in the planar directions, to the face 31 of the back sheet 3 on the absorber 4 side and to the face 32 of the back sheet 3 on the underwear contact side, respectively. At this time, the adhesive 5a and the adhesive 5b applied on the respective surfaces permeate into the back sheet 3 from both the faces. Then, the adhesives 5a and 5b bond to each other inside the back sheet 3. Accordingly, the adhesives 5a and 5b penetrate entirely through the back sheet 3. This improves the interlayer strength of the back sheet 3. In addition, the adhesives 5a and 5b themselves are made resistant to detaching from the back sheet 3.

Here, the predetermined coating regions are intermittent regions in the planar directions where coatings of the first adhesive 5a and the second adhesive 5b are applied. Specifically, the predetermined coating regions are the multiple coating regions 100a of the first adhesive 5a and the multiple coating regions 100b of the second adhesive 5b, which are applied at the interval L in the longitudinal direction of the absorbent article 11 and at the interval W in the width direction of the absorbent article 11.

The coating regions 100a and the coating regions 100b are formed by applications so that the interval between adjacent pairs of the coating region 100a and the coating region 100b may be longer than the maximum length of the fibers of a material (e.g., a nonwoven fabric) for the back sheet 3 in the planar directions. Note that the coating regions 100a of the adhesive 5a and the coating regions 100b of the second adhesive 5b may be shaped like a square or circular.

The adhesives 5a and 5b are applied to the back sheet 3 by the direct coating method. Specifically, the adhesives 5a and 5b are applied by the direct coating method in which the adhesives 5a and 5b are respectively applied onto the face 31 on the absorber 4 side and the face 32 on the underwear side of the back sheet 3 from nozzles of the first roller R1 and nozzles of the second roller R2, while these nozzles are being in direct contact with the faces 31 and 32. In other words, a distance from the nozzle of the first roller R1 to the face 31 of the back sheet 3 on the absorber 4 side and a distance from the nozzle of the second roller R2 to the face 32 of the back sheet 3 on the underwear side are zero. The adhesives 5a and 5b are applied, while in a state of low consistency, to the face 31 of the back sheet 3 on the absorber 4 side and to the face 32 of the back sheet 3 on the underwear side, respectively, by using the direct coating method. Then, the adhesives 5a and 5b permeate into the back sheet 3.

In the back sheet 30 line, the coating regions 100 may be formed so that the areas of the coating regions 100a of the first adhesive 5a at the face 31 of the back sheet 3 on the absorber 4 side may be larger than the areas of the coating regions 100b of the second adhesive 5b at the face 32 of the back sheet 3 on the underwear contact side.

At Step 2 (bonding step), a top sheet line 20 feeding the lengthy top sheet 2, the absorber line 40 feeding the lengthy absorber 4, a waterproof paper sheet line 70 feeding the lengthy waterproof paper sheet 7, the back sheet line 30 feeding the lengthy back sheet 3, and a release paper sheet line 60 feeding the lengthy release paper sheet 6 merge.

Then, a lengthy continuum of the top sheets 2 continuously-fed in the top sheet line 20, the lengthy continuum of the absorbers 4 continuously-fed in the absorber line 40, the lengthy continuum of the back sheets 3 continuously-fed in the back sheet line 30, a lengthy continuum of the waterproof paper sheets 7 continuously-fed in the waterproof paper sheet line 70, and a lengthy continuum of the release paper sheets 6 continuously-fed in the release paper sheet line 60 are bonded to each other. Specifically, the continua of the sheets are stacked and bonded to each other by thermal compression bonding using embossing rollers or ultrasound, or the like. Thus, a lengthy continuum of the absorbent articles 11 is formed.

Here, the waterproof paper sheet 7 is bonded to the back sheet 3 with the adhesive 5a formed on the back sheet 3. In other words, since the coating regions 100a of the adhesive 5a are formed on the face 31 of the back sheet 3 on the absorber 4 side, the waterproof paper sheet 7 can be bonded to the back sheet 3 with the adhesive 5a.

At Step 3 (cutting step), the continuum of the absorbent articles 11 subjected to bonding at Step S2 are cut in a predetermined length.

Specifically, the absorbent article 11 is formed by cutting the continuum of the absorbent articles 11 in a direction (CD) intersecting the MD at a predetermined interval. Note that the predetermined interval is the width-directional dimension of the absorbent article 11.

In the absorbent article 11 according to the second embodiment, coatings of the adhesives 5a and 5b are applied to the coating regions 100 of the adhesive 5 from both the faces of the back sheet 3. The coating regions 100a and 100b are formed by causing the adhesives 5a and 5b to reliably permeate into the back sheet 3. The adhesive 5 fixates the fibers of the back sheet 3 with each other, thereby improving the interlayer strength of the back sheet 3.

As has been described above, in the absorbent article 11 according to the present embodiment, the adhesives 5a and 5b can be prevented from being separated from the back sheet 3 when the absorbent article 11 is peeled off underwear. Moreover, in the absorbent article 11 according to the present embodiment, interlayer separation of the back sheet 3 can be prevented.

The manufacturing method of the absorbent article 11 according to the second embodiment can provide a method of manufacturing the absorbent article 11 in which the adhesives 5a and 5b are prevented from being separated from the back sheet 3 when the absorbent article 11 is peeled off underwear.

In the manufacturing method of the absorbent article 11 according to the second embodiment, with respect to the continuum of the back sheets 3, a coating of the first adhesive 5a is applied from the face 31 of the back sheet 3 on the absorber 4 side by using the first roller R1. Accordingly, the first adhesive 5a applied from the face 31 on the absorber 4 side can be used as an adhesive for bonding the back sheet 3 and the absorber 4 together.

As a result, the manufacturing method of the absorbent article according to the present embodiment does not require a step of applying a coating of an adhesive for bonding the back sheet 3 and the absorber 4 together. This avoids expansion of manufacturing facility and an increase in facility costs.

Other Embodiments

In the embodiments described above, a pantyliner has been described as an example of an absorbent article. However, the present invention is not limited to pantyliners, but is applicable to feminine absorbent articles such as sanitary napkins and incontinence pads, and to diapers.

Hereinabove, the present invention has been described in detail by using the above embodiments. However, it should be apparent for those skilled in the art that the present invention is not limited to the embodiment described herein. The present invention can be implemented in the form of modifications and variations without departing from the spirit and scope of the present invention as defined in the appended claims. It is to be therefore understood that the disclosure herein is for purposes of illustration only and is not intended to limit the scope of the present invention. Furthermore, the embodiments and the modification of the present invention can be combined.

Note that the entire content of Japanese Patent Application No. 2008-119415 (filed on Apr. 30, 2008) is incorporated by reference into this application.

INDUSTRIAL APPLICABILITY

As described above, the present invention can provide an absorbent article and a method of manufacturing the absorbent article which make it possible to present an adhesive from being separated from a back sheet when the absorbent article is peeled off from underwear.

What is claimed is:

1. An absorbent article comprising a water-disintegratable top sheet, a water-disintegratable back sheet composed of nonwoven fabric, and a water-disintegratable absorber interposed between the top sheet and the back sheet, wherein
    adhesive coating regions are formed in the back sheet, and
    the adhesive coating regions are provided to continuously extend from one face of the back sheet to the other face of the back sheet, wherein
    the adhesive coating regions are formed intermittently in planar directions of the back sheet with intervals between adjacent ones of the adhesive coating regions that are longer than a maximum length of fibers in the back sheet, and
    the adhesive coating regions are formed to continuously extend from a face of the back sheet on an absorber side, to a face of the back sheet on a surface side to be in contact with underwear with areas of the adhesive coating regions at the face of the back sheet on the absorber side being larger than areas of the adhesive coating regions at the face of the back sheet on the surface side to be in contact with underwear.

2. The absorbent article according to claim 1 wherein to the adhesive coating regions, a first adhesive is applied from the absorber side of the back sheet, and a second adhesive is applied from the surface side of the back sheet to be in contact with underwear.

3. A method of manufacturing an absorbent article including a water-disintegratable top sheet, a water-disintegratable back sheet, and a water-disintegratable absorber interposed between the top sheet and the back sheet, the method comprising:
    a coating step of applying a first adhesive and a second adhesive to predetermined regions in a continuously-fed lengthy continuum of the back sheets, the first adhesive being applied by a first roller from an absorber side of the back sheet, the second adhesive being applied by a second roller from a surface side of the back sheet to be in contact with underwear; and
    a bonding and cutting step of bonding a continuously-fed lengthy continuum of the top sheets, a continuously-fed lengthy continuum of the absorbents, and the continuum of the back sheets together, and then cutting the continua in a predetermined length.

* * * * *